(12) United States Patent
Inoue et al.

(10) Patent No.: US 8,746,047 B2
(45) Date of Patent: Jun. 10, 2014

(54) DISPERSION ANALYSIS METHOD AND DEVICE

(75) Inventors: Takashi Inoue, Kitanagoya (JP); Joju Niida, Kitanagoya (JP); Yasuki Matsumura, Uji (JP); Kentaro Matsumiya, Kyoto (JP)

(73) Assignee: Pokka Corporation, Aichi (JP)

( * ) Notice: Subject to any disclaimer, the term of this patent is extended or adjusted under 35 U.S.C. 154(b) by 398 days.

(21) Appl. No.: 13/003,975

(22) PCT Filed: Jul. 15, 2009

(86) PCT No.: PCT/JP2009/062833
§ 371 (c)(1),
(2), (4) Date: Jan. 13, 2011

(87) PCT Pub. No.: WO2010/008028
PCT Pub. Date: Jan. 21, 2010

(65) Prior Publication Data
US 2011/0126615 A1 Jun. 2, 2011

(30) Foreign Application Priority Data
Jul. 16, 2008 (JP) .................................. 2008-185414

(51) Int. Cl.
*G01N 1/38* (2006.01)
(52) U.S. Cl.
USPC ....... 73/61.41; 73/61.43; 73/61.44; 73/61.59; 73/61.63; 73/61.71
(58) Field of Classification Search
USPC ...................................................... 73/61.59
See application file for complete search history.

(56) References Cited

U.S. PATENT DOCUMENTS

| 6,466,319 | B2 | 10/2002 | Harris et al. | |
|---|---|---|---|---|
| 6,691,057 | B2 | 2/2004 | Lerche et al. | |
| 2001/0046048 | A1* | 11/2001 | Harris et al. | 356/338 |
| 2004/0011975 | A1 | 1/2004 | Nicoli et al. | |
| 2004/0012782 | A1* | 1/2004 | Mason et al. | 356/338 |
| 2004/0265177 | A1 | 12/2004 | Nicoli et al. | |
| 2005/0021244 | A1 | 1/2005 | Nicoli et al. | |
| 2007/0010974 | A1* | 1/2007 | Nicoli et al. | 702/196 |

FOREIGN PATENT DOCUMENTS

| DE | 4026525 A1 * | 10/1991 | ............ G01N 15/04 |
|---|---|---|---|
| EP | 0 164 807 A2 | 12/1985 | |
| JP | 05-61320 | 1/1986 | |
| JP | 01-213228 | 8/1989 | |

(Continued)

OTHER PUBLICATIONS

English Translation of JP 05107176 A.*

(Continued)

*Primary Examiner* — Hezron E Williams
*Assistant Examiner* — Alexander Mercado
(74) *Attorney, Agent, or Firm* — Seager, Tufte & Wickhem LLC

(57) ABSTRACT

Provided is a method for analyzing a dispersion made by dispersing a liquid or solid dispersoid into a liquid dispersion medium. The method includes the steps of: preparing a sample liquid from the dispersion by forming an agglomerate of the dispersoid in the dispersion medium; redispersing the dispersoid that forms the agglomerate in the sample liquid into the dispersion medium of the sample liquid; and measuring the amount of the dispersoid that has been redispersed from the agglomerate in the sample liquid.

5 Claims, 4 Drawing Sheets

(56) References Cited

FOREIGN PATENT DOCUMENTS

| JP | 05-107176 | | 4/1993 | |
|---|---|---|---|---|
| JP | 05107176 A | * | 4/1993 | ............ G01N 15/02 |
| JP | 2002-125588 | | 5/2002 | |
| JP | 2005-536721 | | 2/2005 | |
| JP | 2005-138062 | | 6/2005 | |
| JP | 2005138062 A | * | 6/2005 | ........... B01D 17/022 |
| JP | 2006-527854 | | 7/2006 | |
| JP | 2006-349385 | | 12/2006 | |
| WO | 2004/009733 A2 | | 1/2004 | |
| WO | 2005/001471 A1 | | 1/2005 | |

OTHER PUBLICATIONS

English Translation of JP 2005138062 A.*

"International Preliminary Report on Patentability for International Application No. PCT/JP2009/062833," Authorized officer: Gijsbertus Beijer from the International Bureau of WIPO, issued on Feb. 8, 2011. 6 pages.

* cited by examiner

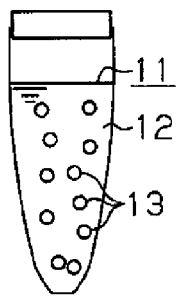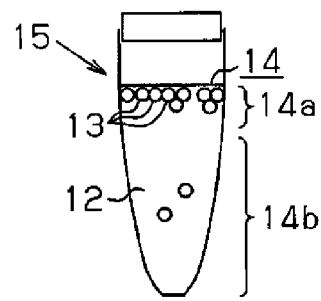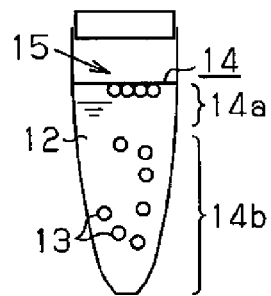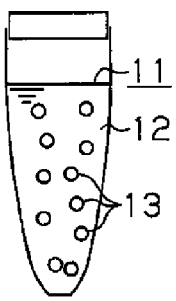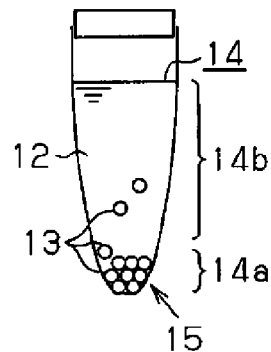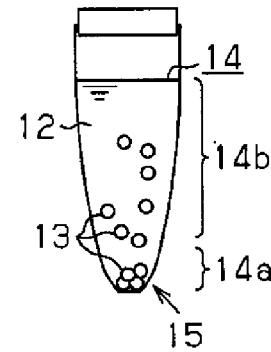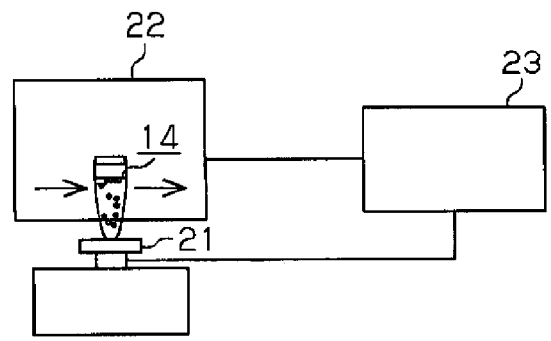

DISPERSION ANALYSIS METHOD AND DEVICE

TECHNICAL FIELD

The present invention relates to a dispersion analysis method, a dispersion analysis device, a dispersion stability evaluation method, and a dispersion stability evaluation device.

BACKGROUND ART

Dispersions made by dispersing a liquid or solid dispersoid in a liquid dispersion medium are used for products such as foods, beverages, cosmetics, paints, fuel, and pharmaceuticals. To secure the quality of such products, dispersion stability is an important element.

Patent Document 1 describes a dispersion stability evaluation by comparing the turbidity of a dispersion made by dispersing asphaltene in a mineral oil with the turbidity of a sample solution obtained by centrifuging the dispersion. Patent Document 2 describes a method for evaluating the stability of a sample containing a particle dispersion body by forming particles in the dispersion body into a massive state and by detecting an increase in the massive-state particles. Patent Document 3 describes evaluation of redispersibility of cream contained in milk tea by visually observing a state when the milk tea is shaken. Patent Document 4 describes redispersion of drugs contained in an aqueous suspension eye drop. More specifically, Patent Document 4 describes an evaluation of redispersibility of drugs by rotating a container containing the aqueous suspension eye drop so as to redisperse the drugs in the aqueous suspension eye drop, and counting the number of rotations, which permit uniform redispersion of the drugs.

Techniques for analyzing the quality of dispersions are important for shortening the time of developing products using dispersions and stabilizing the quality of the products. In particular, since the state of an agglomerate of a dispersoid formed in a dispersion is deeply related to the dispersion state of the dispersion, its analysis is important. However, practical propositions as to a technique for quantitatively analyzing the state of an agglomerate of a dispersoid, and a quantitative evaluation technique based on the state of the agglomerate have not been made to date.

In the technique described in Patent Document 1, although it is possible to obtain findings as to how easily separation (precipitation) generated by the density difference between a dispersion medium and a dispersoid occurs, any findings as to the state of an agglomerate of a dispersoid cannot be obtained. In the technique described in Patent Document 2, although it is possible to obtain findings as to how easily particles agglomerate, any findings as to the state of an agglomerate of a dispersoid cannot be obtained. The technique described in Patent Document 3 poses a problem that it is difficult to apply this technique to dispersions in which dispersoid is difficult to be visually recognized. Furthermore, determination based on visual observation as described in Patent Document 3 may be inadequate for quantitative analysis technique required in product development, or analysis technique for determining the product quality. For the same reason, the technique described in Patent Document 4 may be inadequate as an analysis technique since a state in which drugs in an aqueous suspension eye drop are uniformly redispersed is determined by visual observation.

PRIOR ART DOCUMENTS

Patent Document 1: Japanese Examined Patent Publication No. 05-061320
Patent Document 2: Japanese National Phase Laid-Open Patent Publication No. 2006-527854
Patent Document 3: Japanese Laid-Open Patent Publication No. 2002-125588
Patent Document 4: Japanese Examined Patent Publication No. 07-096495

SUMMARY OF INVENTION

Problems that the Invention is to Solve

It is therefore an object of the present invention to provide a method and a device useful for quantitatively analyzing the state of an agglomerate of a dispersoid in a dispersion, as well as a method and a device useful for quantitatively evaluating the dispersion stability.

Means for Solving the Problems

In order to achieve the above-mentioned object, a first aspect of the present invention provides a method for analyzing a dispersion made by dispersing a liquid or solid dispersoid into a liquid dispersion medium. The method includes the steps of: preparing a sample liquid from the dispersion by forming an agglomerate of the dispersoid in the dispersion medium; redispersing the dispersoid that forms the agglomerate in the sample liquid into the dispersion medium of the sample liquid; and measuring the amount of the dispersoid that has been redispersed from the agglomerate in the sample liquid.

A second aspect of the present invention provides a device for analyzing the dispersion. The device includes: redispersion means for redispersing the dispersoid that forms an agglomerate in a sample liquid, which is prepared from the dispersion, into the dispersion medium of the sample liquid; and measurement means for measuring the amount of the dispersoid that has been redispersed by the redispersion means.

A third aspect of the present invention provides a method for evaluating the stability of the dispersion. The method includes the steps of: preparing a sample liquid from the dispersion by forming an agglomerate of the dispersoid in the dispersion medium; redispersing the dispersoid that forms the agglomerate in the sample liquid into the dispersion medium of the sample liquid; and measuring the amount of the dispersoid that has been redispersed from the agglomerate in the sample liquid. In the method, the stability of the dispersion is evaluated based on the measured amount of the redispersed dispersoid.

A fourth aspect of the present invention provides a device for evaluating the stability of the dispersion. The device includes: redispersion means for redispersing the dispersoid that forms an agglomerate in a sample liquid, which is prepared from the dispersion, into the dispersion medium of the sample liquid; and measurement means for measuring the amount of the dispersoid that has been redispersed by the redispersion means. In the method, the stability of the dispersion is evaluated based on the measured amount of the redispersed dispersoid.

BRIEF DESCRIPTION OF DRAWINGS

FIG. 1(*a*) is a diagram schematically showing a dispersion;
FIG. 1(*b*) is a diagram schematically showing a sample liquid in which an agglomerate of a dispersoid is floating;

FIG. 1(c) is a diagram schematically showing a state in which the agglomerate in the sample liquid in FIG. 1(b) is redispersed;

FIG. 2(a) is a diagram schematically showing a dispersion;

FIG. 2(b) is a diagram schematically showing a sample liquid in which an agglomerate of a dispersoid sinks;

FIG. 2(c) is a diagram schematically showing a state in which the agglomerate in the sample liquid in FIG. 2(b) is redispersed;

FIG. 3 is a schematic view showing an analysis device and a stability evaluation device of the present embodiment;

MODE FOR CARRYING OUT THE INVENTION

Figure 4A:
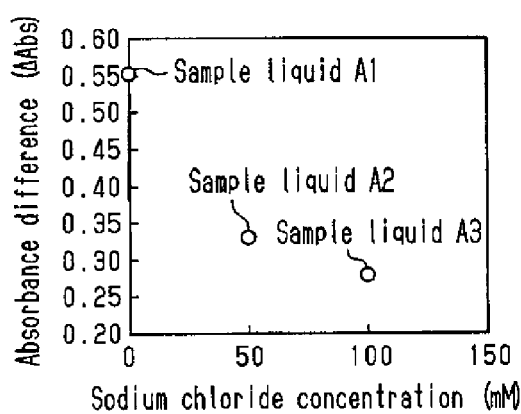
FIG. 4(a) is a graph showing the relationship between the sodium chloride concentration and the absorbance difference in the sample liquids A1 to A3.

Hereinafter, specific embodiments of the present invention will be described in detail with reference to FIGS. 1 to 3.
<Dispersion Analysis Method>

As shown in FIGS. 1(a) and 2(a), a dispersion 11 is made by dispersing a liquid or solid dispersoid 13 in a liquid dispersion medium 12. As shown in FIGS. 1(b) and 2(b), a sample liquid 14 is prepared from the dispersion 11 by forming an agglomerate 15 of the dispersoid 13 in the dispersion medium 12. In an analysis method of the present embodiment, the sample liquid 14 prepared from the dispersion 11 is used. The analysis method includes the steps of: redispersing the dispersoid 13 that forms the agglomerate 15 in the sample liquid 14 into the dispersion medium 12 of the sample liquid 14; and measuring the amount of the dispersoid 13 that has been redispersed into the dispersion medium 12.
Dispersion The dispersion 11 may be an emulsion (liquid emulsion, emulsified liquid, or milky liquid) and may be a suspension (liquid suspension). The color tone of the dispersion 11 is not particularly limited.

An emulsion is a dispersion system in which liquid dispersoid is dispersed as minute liquid particles (droplets) in a liquid dispersion medium. The dispersion medium may be water based or oil based. The dispersoid also may be water based or oil based. The dispersion medium and the dispersoid are each formed of one material or a plurality of materials. The emulsion includes an O/W emulsion, a W/O emulsion, an O/W/O emulsion, and a W/O/W emulsion. The emulsion is generally formed by using an emulsifier. The emulsion is used in various fields such as of foods, beverages, cosmetics, fuel, pharmaceuticals, and adhesive agents. The stability of the emulsion is affected by, for example, types of emulsifiers to be used, and emulsifying methods.

A suspension is a dispersion system in which solid dispersoid is dispersed as minute solid particles in a liquid dispersion medium. The dispersion medium may be water based or oil based. The dispersoid may be formed of inorganic materials such as metal, ceramic, and clay, or may be formed of organic materials such as synthetic resin and rubber. The dispersion medium and the dispersoid are each formed of one material or a plurality of materials. Similar to the emulsion, the suspension is used in various fields such as of foods, beverages, cosmetics, fuel, pharmaceuticals, paints, ink, adhesive agents, and fillers for resin.

Since the dispersed state of the dispersion 11 affects the stability of products using the dispersion 11 when they are stored or used and affects functions exhibited by the dispersoid 13, the dispersed state is extremely important in quality of such products.
Sample Liquid As shown in FIGS. 1(b) and 2(b), the sample liquid 14 contains an agglomerate 15 in which particles of the dispersoid 13 agglomerate or flocculate. Therefore, the sample liquid 14 includes a high concentration region 14a, in which the dispersoid 13 is present at relatively high concentration, and a low concentration region 14b, in which the dispersoid 13 is present at relatively low concentration. The dispersoid 13 that forms the agglomerate 15 can be redispersed into a dispersion medium 12. The sample liquid 14 may contain at least one of an aggregate in which particles of the dispersoid 13 aggregate and a coagulate in which particles of the dispersoid 13 coagulate.

In the sample liquid 14 shown in FIG. 1(b), the agglomerate 15 is floating in the sample liquid 14. In the sample liquid 14 shown in FIG. 2(b), the agglomerate 15 sinks in the sample liquid 14. The agglomerate 15 is generated when the attractive force between particles of the dispersoid 13 is larger than the repulsive force between the particles. The dispersoid 13 is dispersed in the dispersion medium 12, for example, by electrical repulsion by charge of particles of the dispersoid 13, or by steric repulsion by macromolecules adsorbed on particles of the dispersoid 13. When the dispersoid 13 in the dispersion 11 is dispersed by the electrical repulsion, the agglomerate 15 is formed by, for example, adjusting pH or the electrolyte concentration of the dispersion 11 to cancel the surface electric charge on particles of the dispersoid 13. When dispersoid 13 is dispersed by the steric repulsion, the agglomerate 15 is formed by, for example, changing the temperature of the dispersion 11.

Furthermore, regardless of how the dispersoid 13 in the dispersion 11 disperses, the formation of the agglomerate 15 can also be carried out by subjecting the dispersion 11 to centrifugation, that is, by applying an acceleration that is larger than the acceleration of gravity to the dispersion 11. The method using centrifugation is advantageous because the condition for forming the agglomerate 15 can be set easily, and composition change of the dispersion 11 can be suppressed. The agglomerate 15 may be formed not only by one method but also by a plurality of methods.
Redispersion of Dispersoid As mentioned above, in analyzing the dispersion 11, the dispersoid 13 that forms the agglomerate 15 in the sample liquid 14 is redispersed into the dispersion medium 12 of the sample liquid 14. As a result, as shown in FIGS. 1(c) and 2(c), while the concentration of the dispersoid 13 in the high concentration region 14a of the sample liquid 14 is reduced, the concentration of the dispersoid 13 in the low concentration region 14b is increased.

The dispersoid 13 is redispersed by, for example, propagating vibration to the sample liquid 14 from outside the sample liquid 14, or forming a temperature gradient in the sample liquid 14 to generate Marangoni convection in the sample liquid 14, or by pseudo gravity made by using the centrifugal force to generate natural convection in the sample liquid 14, or by stirring the sample liquid 14 with a rotor or a stirring rod provided to a stirrer. As the method to be used for redispersion, not necessarily one method but a plurality of methods may be employed. However, a method using vibration is advantageous because it can easily apply a constant energy to the agglomerate 15. In this method, by applying vibration energy to the agglomerate 15, the particle motion of the dispersoid 13 is activated. As a result, redispersion of the dispersoid 13 that forms the agglomerate 15 occurs. Therefore, if the energy to be applied is made to be constant, the substantially linear relationship is satisfied between time during which the energy is applied and the amount of redispersed dispersoid 13.

The vibration to be propagated to the sample liquid 14 may be vibration by a vibration exciter such as a vortex mixer, or waves such as sound wave, ultrasonic wave, low frequency wave, and electromagnetic wave. The method using a vibration exciter is advantageous because energy can be applied to the agglomerate 15 rapidly. The method using a wave is advantageous because energy can be applied to the agglomerate 15 in a state in which a container accommodating the sample liquid 14 is not brought into contact with a wave source. The vibration propagated to the sample liquid 14 may be a sinusoidal wave or may be a random wave. However, the sinusoidal wave is advantageous because it can easily apply a constant energy to the agglomerate 15. The propagation of sinusoidal vibration to the sample liquid 14 is carried out by, for example, using an electromagnetic vibration exciter that outputs sinusoidal vibration in response to receiving input from a transmitter.

The weaker the degree of agglomeration, the more likely that the redispersion of the dispersoid 13 occurs. For example, in the agglomerate 15 in which particles of the dispersoid 13 flocculate, as compared with the agglomerate 15 in which particles of the dispersoid 13 agglomerate, the degree of agglomeration of particles of the dispersoid 13 is weaker, that is to say, an attractive force that acts on the particles of the dispersoid 13 is weaker. Therefore, redispersion of the dispersoid 13 occurs more easily. However, in the same agglomerate 15 in which particles of the dispersoid 13 agglomerate or flocculate, there is a difference in the attractive forces acting on the particles of the dispersoid 13, that is, a difference in the degree of agglomeration of the particles of the dispersoid 13. Such a difference in the degree of agglomeration is reflected on how easily redispersion of dispersoid 13 occurs.

Measurement of Redispersed Dispersoid

The dispersoid 13 that forms the agglomerate 15 in the sample liquid 14 is redispersed into the dispersion medium 12 of the sample liquid 14, and then, the amount of the dispersoid 13 that has been redispersed into the dispersion medium 12 is measured. In the sample liquid 14 prepared in the same condition from the dispersion 11 whose dispersion state is different, even if the type of the dispersoid 13 is the same, it is predicted that the degree of agglomeration of particles of the dispersoid 13 in the agglomerate 15 will be different. The difference in the degree of agglomeration can be found out from the amount of the redispersed dispersoid 13 to be measured when the condition for redispersing the dispersoid 13 and the condition for measuring the redispersed dispersoid 13 are made to be the same. That is to say, the amount of the redispersed dispersoid 13 to be measured herein is a quantitative index representing the degree of agglomeration of particles of the dispersoid 13 in the agglomerate 15 in the sample liquid 14.

The amount of the redispersed dispersoid 13 may be measured not only directly, but also indirectly. When the amount of the redispersed dispersoid 13 is indirectly measured, for example, at least one parameter selected from the absorbance, transmitted light, reflected light, fluorescence, dielectric constant, electric conductivity, sugar content, and differential refractive index is used. The amount of the redispersed dispersoid 13 may be measured as a converted value on the basis of the value of at least one parameter that has been preliminarily measured by a predetermined dispersion 11.

It is preferable that the amount of the redispersed dispersoid 13 be calculated as a ratio with respect to the total amount of the dispersoid 13 in the dispersion 11, and it is preferable that the change of the ratio over time be also measured. When such a change over time is measured, it is possible to obtain a quantitative index according to the degree of agglomeration of particles of the dispersoid 13 in the agglomerate 15 without depending upon the concentration of the dispersoid 13.

<Dispersion Stability Evaluation Method>

In the evaluation method in the present embodiment, the stability of the dispersion 11 is evaluated based on the amount of the redispersed dispersoid 13 measured as mentioned above. For example, when the amounts of the redispersed dispersoid 13 measured by using the sample liquids 14 that are respectively prepared from a plurality of dispersions 11 are compared with each other, superiority or inferiority of the stability of each dispersions 11 can be evaluated quantitatively. Furthermore, when the amount of the redispersed dispersoid 13, which is measured by using a dispersion 11 that is a subject of the stability evaluation, is compared with the amount of the redispersed dispersoid 13, which is measured by using a dispersion 11 on the acceptable level, the acceptability of the stability of the dispersion 11 can be determined. According to this evaluation method, since the stability of the dispersion 11 can be evaluated quantitatively based on the agglomeration force between particles of the dispersoid 13, this method is useful for determining the quality of products using the dispersion 11.

<Dispersion Analysis Device>

An analysis device of the present embodiment analyzes a dispersion 11 based on information obtained from a sample liquid 14. The analysis device includes: redispersion means (a redispersion section) for redispersing a dispersoid 13 that forms an agglomerate 15 in the sample liquid 14 into a dispersion medium 12 of the sample liquid 14; and measurement means (a measurement section) for measuring the amount of the dispersoid 13 that has been redispersed by the redispersion means. More specifically, the analysis device includes, as shown in FIG. 3, a speaker 21 for propagating a sound wave to the sample liquid 14 from outside the sample liquid 14, a spectrophotometer 22 for measuring the absorbance of a low concentration region 14b of the sample liquid 14, and a computer 23 for controlling the speaker 21 and the spectrophotometer 22. The speaker 21, together with the computer 23, constitutes the redispersion means. The spectrophotometer 22, together with the computer 23, constitutes the measurement means. The computer 23 includes a control section (CPU) and a storage section (RAM, ROM, and the like). The computer 23 is electrically connected to the speaker 21 and the spectrophotometer 22.

The dispersoid 13 forming the agglomerate 15 in the sample liquid 14 is gradually redispersed when the sound wave from the speaker 21 is propagated to the sample liquid 14. The waveform of the sound wave generated from the speaker 21 is a sinusoidal wave, and the frequency depends upon a value set by using input means (not shown) such as a keyboard and a mouse of the computer 23. After vibration by the sound wave is propagated to the sample liquid 14 for a predetermined time by using the speaker 21, the amount of the dispersoid 13 that has been redispersed into the dispersion medium 12 of the sample liquid 14 is measured by using the spectrophotometer 22. Specifically, monochromatic light transmitting the sample liquid 14 is detected by the spectrophotometer 22, and the detected signal is input into the computer 23 via an amplifier and an A/D converter. The computer 23 calculates the absorbance of the sample liquid 14 based on the input signal, and the calculation results are displayed as a measurement value related to the amount of the redispersed dispersoid 13 on a display (not shown).

When the measurement of the absorbance is carried out a plurality of times, a plurality of the resultant measurement values are stored in the storage section of the computer 23. The computer 23 may be capable of displaying the change of the measurement values over time in a graph on the display.

Instead of the speaker 21, the analysis device may include a heater, a turntable, a stirrer with a rotor or a stirring rod, a vibration exciter, an ultrasonic wave generator, or an electromagnetic wave generator. The spectrophotometer 22 may measure the transmittance instead of the absorbance. The analysis device may include, instead of the spectrophotometer 22, a reflective photometer, a fluorophotometer, a dielectric constant measurement device, an electric conductivity measurement device, a sugar content measurement device, or a differential refractive index measurement device.

<Dispersion Stability Evaluation Device>

A stability evaluation device of the present embodiment evaluates the stability of the dispersion 11 based on information obtained from the sample liquid 14. The stability evaluation device includes: redispersion means (a redispersion section) for redispersing the dispersoid 13 that forms the agglomerate 15 in the sample liquid 14 into the dispersion medium 12 of the sample liquid 14; and measurement means (a measurement section) for measuring the amount of the dispersoid 13 redispersed by the redispersion means, and evaluates the stability of the dispersion 11 based on the measurement value measured by the measurement means. Hereinafter, the stability evaluation device is described mainly as to the points that are different from the above-mentioned analysis device.

In the stability evaluation device, the storage section of the computer 23 stores a plurality of measurement values. Therefore, by comparing the measurement values measured in the sample liquids 14 respectively prepared from the various dispersions 11, superiority or inferiority of the stability of each dispersion 11 can be evaluated quantitatively. Furthermore, when the measurement value measured in a sample liquid 14 prepared from a dispersion 11, which is on the acceptability level, is stored as a reference value in the storage section, the measurement value measured in a sample liquid 14 prepared from a dispersion 11 that is a subject of stability evaluation can be compared with the reference value.

The present embodiment has the following advantages.

According to the method and device of the present embodiment, a dispersoid 13 forming an agglomerate 15 in a sample liquid 14 is redispersed into a dispersion medium 12 of the sample liquid 14, and then the amount of the dispersoid 13 that has been redispersed into the dispersion medium 12 is measured. Since the amount of the redispersed dispersoid 13 to be measured depends upon the degree of agglomeration of particles of the dispersoid 13 in the agglomerate 15, the method and device are useful for quantitatively determining the state of the agglomerate 15. In particular, when the amount of the redispersed dispersoid 13 is measured at a plurality of different timings, the method and device are useful to quantitatively determine the degree of agglomeration of particles of the dispersoid 13 in the agglomerate 15 based on the redispersion rate calculated from the change of the measurement values over time. The analysis permits obtaining the findings as to the condition of the dispersion 11 in which particles of the dispersoid 13 are dispersed excellently, the condition of the dispersion 11 in which particles of the dispersoid 13 agglomerate or flocculate in such a manner that they can be redispersed, and the condition of the dispersion 11 in which particles of the dispersoid 13 aggregate or coagulate in such a manner that they cannot be redispersed. This is useful for considering the composition condition and manufacturing condition for obtaining various dispersions, and the storing condition and using condition. Therefore, the method and device of the present embodiment have high usefulness in evaluating the quality of products using the dispersion 11. For example, when a composition is changed in a product using the dispersion 11 it is possible to determine whether or not the quality of the product can be maintained at a satisfactory level based on the findings obtained by the method and device of the present embodiment. Furthermore, in order to obtain a dispersion having a specific function obtained when particles of the dispersoid 13 agglomerate or flocculate, it is possible to consider, based on the findings obtained by the method and device of the present embodiment, the composition condition and manufacturing condition for obtaining dispersions, in which agglomeration or flocculation easily occurs, and the storing condition and using condition.

Analysis of the dispersion 11 is carried out based on information obtained from the sample liquid 14. More specifically, it is carried out by measuring the amount of the dispersoid 13 redispersed from the agglomerate 15 in the sample liquid 14. Therefore, an objective and quantitative analysis without depending upon the property such as appearance of the dispersion 11 can be carried out. For example, even if the dispersion 11 is colored, by selecting appropriate means for measuring the amount of the redispersed dispersoid 13, analysis of the dispersion 11 can be appropriately carried out.

When redispersion of the dispersoid 13 is carried out by propagating vibration to the sample liquid 14 from outside the sample liquid 14, energy for generating redispersion of the dispersoid 13 can be uniformly applied to the agglomerate 15 easily as compared with the case where the redispersion is carried out by other methods. Furthermore, the temperature change of the sample liquid 14 is small. This is advantageous in carrying out an analysis of the dispersion 11 with high reproducibility.

When the vibration propagated to the sample liquid 14 is a sinusoidal wave with a constant frequency, conditions in redispersing the dispersoid 13 is less likely to vary as compared with other cases. This is advantageous in carrying out an analysis of the dispersion 11 with high reproducibility.

When the amount of the dispersoid 13 redispersed from the agglomerate 15 in the sample liquid 14 is calculated as a ratio with respect to the total amount of the dispersoid 13 in the dispersion 11, and the ratio is measured over time, it is possible to obtain the index according to the degree of agglomeration of particles of the dispersoid 13 in the agglomerate 15 without depending upon the concentration of the dispersoid 13.

In preparation of the sample liquid 14 from the dispersion 11, when the agglomerate 15 is formed by subjecting the dispersion 11 to centrifugation, the condition for forming the agglomerate 15 can be easily set and composition change of the dispersion 11 can be suppressed, as compared with other methods. This is advantageous in carrying out an analysis of the dispersion 11 with high reproducibility.

Next, the present invention is described further specifically with reference to Examples.

EXAMPLE 1

Preparation of Emulsified Liquids A1 to A3

With 200 mM of phosphate buffer solution that had been adjusted to pH 7.0, 0.5% by mass of bovine serum albumin (BSA) and 2.5% by mass of corn oil were mixed. By homogenizing the mixture by using a homogenizer, a preliminary emulsified liquid was prepared. To a sample tube, 240 µL of the resultant preliminary emulsified liquid and 960 µL of pure water were dispensed and then mixed, and thus an emulsified liquid A1 containing 0.5% by mass of corn oil and having a sodium chloride concentration of 0 mM was prepared.

A sodium chloride solution was prepared by dissolving 0.183 g of sodium chloride in 50 mL of pure water. By mixing 960 µL of the sodium chloride solution with 240 µL of the previously obtained preliminary emulsified liquid, an emulsified liquid A2 containing 0.5% by mass of corn oil and having a sodium chloride concentration of 50 mM was prepared.

A sodium chloride solution was prepared by dissolving 0.366 g of sodium chloride in 50 mL of pure water. By mixing 960 µL of the sodium chloride solution with 240 µL of the previously obtained preliminary emulsified liquid, an emulsified liquid A3 containing 0.5% by mass of corn oil and having a sodium chloride concentration of 100 mM was prepared.

The obtained emulsified liquids A1 to A3 were each heat-treated by being immersed in a water bath at 90° C. for 30 minutes together with a sample tube that contained the emulsified liquid.

<Preparation of Sample Liquids A1 to A3>

The emulsified liquids A1 to A3 contained in the sample tubes were centrifuged at 20° C. at 140,000×g for 20 minutes so as to prepare sample liquids A1 to A3. In each sample liquid, it was confirmed that oil drops were agglomerated in the vicinity of the liquid surface of the sample liquid.

<Redispersion of Oil Drops>

Sinusoidal sound wave vibration at 100 Hz was applied to the sample liquids in the sample tubes for one hour by using a speaker (GY-1), produced by Foster Electric Company, Limited, thereby redispersing the agglomerated oil drops.

<Measurement of Redispersion>

Before and after redispersion of oil drops, a part of each sample liquid was collected from the sample tube by using a microsyringe, and it was two-fold diluted with distilled water. In each sample liquid after dilution, the absorbance at a wavelength of 600 nm was measured by using a spectrophotometer (U-2000), produced by Hitachi, Ltd. The reason why a wavelength of 600 nm was selected was because it is useful for measurement of white turbidity of each sample liquid, which is increased by redispersion of oil drops. The average value (n=3) of the differences in the absorbance of each sample liquid measured before and after the redispersion was calculated. The results are shown in Table 1 and FIG. 4(a).

TABLE 1

|  | Sample liquid A1 | Sample liquid A2 | Sample liquid A3 |
|---|---|---|---|
| Sodium chloride concentration (mM) | 0 | 50 | 100 |
| Absorbance difference (ΔAbs) | 0.5521 | 0.3300 | 0.2802 |

As is apparent from the results shown in Table 1 and FIG. 4(a), it was confirmed that the sodium chloride concentration and the absorbance difference (ΔAbs) were correlated with each other. It is thought that the smaller the value of the absorbance difference, the stronger becomes the degree of agglomeration of oil drops agglomerated in the sample liquid, i.e., an agglomerate. Therefore, this reveals that the higher the sodium chloride concentration, the more easily an agglomerate having the stronger degree of agglomeration is formed.

EXAMPLE 2

Preparation of Emulsified Liquids A4 and A5

The emulsified liquid A4 is the same as the emulsified liquid A1 of Example 1. That is to say, the emulsified liquid A4 was prepared by the same method as for the emulsified liquid A1 in Example 1.

The emulsified liquid A5 is the same as the emulsified liquid A3 of Example 1. That is to say, the emulsified liquid A5 was prepared by the same method as for the emulsified liquid A3 in Example 1.

<Preparation of Sample Liquids A4 and A5>

The emulsified liquids A4 and A5 contained in sample tubes were centrifuged at 20° C. at 140,000×g for 20 minutes so as to prepare sample liquids A4 and A5. In each sample liquid, it was confirmed that oil drops were agglomerated in the vicinity of the liquid surface of the sample liquid.

<Redispersion of Oil Drops>

Sinusoidal sound wave vibration at 100 Hz was applied to the sample liquids A4 and A5 in the sample tubes for 20 minutes, 40 minutes, or 60 minutes by using a speaker (GY-1), produced by Foster Electric Company, Limited, thereby redispersing the agglomerated oil drops.

<Measurement of Redispersion>

Before and after redispersion of oil drops, a part of each of the sample liquids A4 and A5 was collected from the sample tube by using a microsyringe, and it was two-fold diluted with distilled water. In each sample liquid after dilution, the average value (n=3) of the absorbance at a wavelength of 600 nm was measured by using a spectrophotometer (U-2000), produced by Hitachi, Ltd. The results are shown in Table 2 and FIG. 4(b).

TABLE 2

|  | Sample liquid A4 | | | |
|---|---|---|---|---|
| Sodium chloride concentration (mM) | 0 | | | |
| Vibration time (minutes) | 0 | 20 | 40 | 60 |
| Absorbance | 0.0249 | 0.2694 | 0.4859 | 0.5633 |
|  | Sample liquid A5 | | | |
| Sodium chloride concentration (mM) | 100 | | | |

TABLE 2-continued

| Vibration time (minutes) | 0 | 20 | 40 | 60 |
|---|---|---|---|---|
| Absorbance | 0.0193 | 0.1527 | 0.2813 | 0.2914 |

Figure 4B:
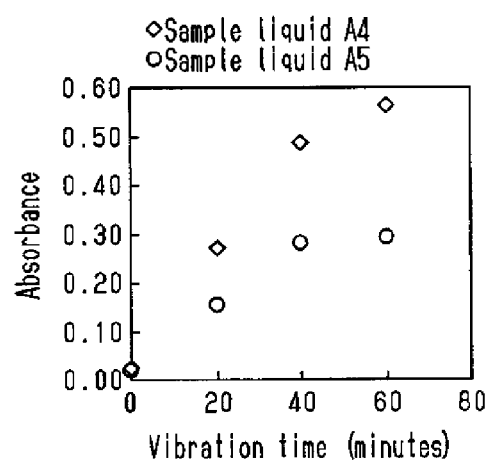
FIG. 4(b) is a graph showing the relationship between the vibration time and the absorbance in the sample liquids A4 and A5.

As is apparent from the results shown in Table 2 and FIG. 4(b), it was confirmed that the longer the time of applying vibration to the sample liquid, the higher became the absorbance of the sample liquid. With reference to FIG. 4(b), it is shown that when the vibration time was 40 minutes or less, the absorbance and the vibration time were almost directly proportional to each other. Therefore, for example, by determining the inclination of the direct proportional line by linear approximation, it is possible to evaluate the degree of agglomeration of the agglomerate in each sample liquid and the dispersion stability.

EXAMPLE 3

Preparation of Emulsified Liquids A6 and A7

The emulsified liquid A6 is the same as the emulsified liquid A1 of Example 1. That is to say, the emulsified liquid A6 was prepared by the same method as for the emulsified liquid A1 in Example 1.

The emulsified liquid A7 is the same as the emulsified liquid A3 of Example 1. That is to say, the emulsified liquid A7 was prepared by the same method as for the emulsified liquid A3 in Example 1.

<Preparation of Sample Liquids A6 and A7>

The emulsified liquids A6 and A7 contained in sample tubes were centrifuged at 20° C. at 140,000×g for 20 minutes so as to prepare sample liquids A6 and A7. In each sample liquid, it was confirmed that oil drops were agglomerated in the vicinity of the liquid surface of the sample liquid.

<Redispersion of Oil Drops>

Rotational vibration was applied to the sample liquids A6 and A7 in the sample tubes for one minute or two minutes by using a vortex mixer (Automatic Lab-mixer HM-10H), produced by IUCHI as a vibration exciter while the number of rotations was set at a scale of 3. Thus, the agglomerated oil drops were redispersed.

<Measurement of Redispersion>

Before and after redispersion of oil drops, a part of each of the sample liquids A6 and A7 was collected from the sample tube by using a microsyringe, and it was eight-fold diluted with distilled water. In each sample liquid after dilution, the average value (n=3) of the absorbance at a wavelength of 600 nm was measured by using a spectrophotometer (U-2000), produced by Hitachi, Ltd. The results are shown in Table 3 and FIG. 5(a).

TABLE 3

| | Sample liquid A6 | | |
|---|---|---|---|
| Sodium chloride concentration (mM) | 0 | | |
| Vibration time (minutes) | 0 | 1 | 2 |
| Absorbance | 0.0249 | 0.2831 | 0.3333 |
| | Sample liquid A7 | | |
| Sodium chloride concentration (mM) | 100 | | |
| Vibration time (minutes) | 0 | 1 | 2 |
| Absorbance | 0.0249 | 0.1640 | 0.1961 |

Figure 5A:
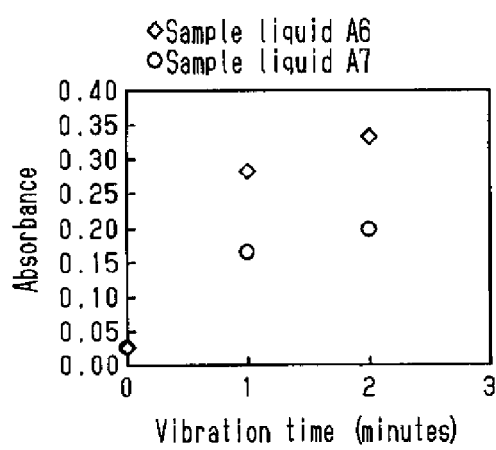
FIG. 5(a) is a graph showing the relationship between the vibration time and the absorbance in the sample liquids A6 and A7.

As is apparent from the results shown in Table 3 and FIG. 5(a), it was confirmed that the longer the time of applying vibration to the sample liquid, the higher became the absorbance of the sample liquid.

EXAMPLE 4

Preparation of Emulsified Liquids A8 and A9

The emulsified liquid A8 is the same as the emulsified liquid A1 of Example 1. That is to say, the emulsified liquid A8 was prepared by the same method as for the emulsified liquid A1 in Example 1.

The emulsified liquid A9 is the same as the emulsified liquid A3 of Example 1. That is to say, the emulsified liquid A9 was prepared by the same method as for the emulsified liquid A3 in Example 1.

<Preparation of Sample Liquids A8 and A9>

The emulsified liquids A8 and A9 contained in sample tubes were centrifuged at 20° C. at 12,000×g for 30 minutes so as to prepare sample liquids A8 and A9. In each sample liquid, it was confirmed that oil drops were agglomerated in the vicinity of the liquid surface of the sample liquid.

<Redispersion of Oil Drops>

Rotational vibration was applied to the sample liquids A8 and A9 in the sample tubes for one minute or two minutes by using a vortex mixer (Automatic Lab-mixer HM-10H), produced by IUCHI as a vibration exciter while the number of rotations was set at a scale of 3. Thus, the agglomerated oil drops were redispersed.

<Measurement of Redispersion>

Before and after redispersion of oil drops, a part of each of the sample liquids A8 and A9 was collected from the sample tube by using a microsyringe, and it was three-fold diluted with distilled water. In each sample liquid after dilution, the average value (n=3) of the absorbance at a wavelength of 600 nm was measured by using a spectrophotometer (U-2000), produced by Hitachi, Ltd. The results are shown in Table 4 and FIG. 5(b).

TABLE 4

| | Sample liquid A8 | | |
|---|---|---|---|
| Sodium chloride concentration (mM) | 0 | | |
| Vibration time (minutes) | 0 | 1 | 2 |
| Absorbance | 0.0080 | 0.2200 | 0.2600 |
| | Sample liquid A9 | | |
| Sodium chloride concentration (mM) | 100 | | |
| Vibration time (minutes) | 0 | 1 | 2 |
| Absorbance | 0.0200 | 0.1210 | 0.2290 |

Figure 5B:
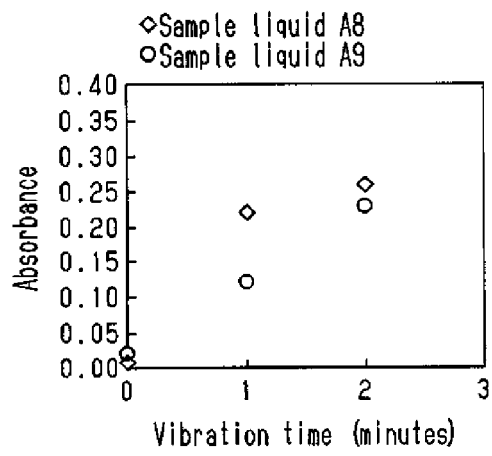
FIG. 5(b) is a graph showing the relationship between the vibration time and the absorbance in the sample liquids A8 and A9.

As is apparent from the results shown in Table 4 and FIG. 5(b), it was confirmed that the longer the time of applying vibration to the sample liquid, the higher became the absorbance of the sample liquid.

EXAMPLE 5

Preparation of Emulsified Liquids A10 and A11

With 200 mM of phosphate buffer solution that had been adjusted to pH 7.0, 0.5% by mass of bovine serum albumin (BSA) and 2.5% by mass of corn oil were mixed. By homogenizing the mixture by using a homogenizer, a preliminary emulsified liquid was prepared. To a 500 mL-centrifuge tube, 50 mL of the resultant preliminary emulsified liquid and 200 mL of pure water were dispensed and then mixed. Thus, an emulsified liquid A10 with a sodium chloride concentration of 0 mM was prepared.

A sodium chloride solution was prepared by dissolving 1.463 g of sodium chloride in 200 mL of pure water. By mixing 200 mL of the sodium chloride solution with 50 mL of the previously obtained preliminary emulsified liquid, an emulsified liquid A11 with a sodium chloride concentration of 100 mM was prepared.

The obtained emulsified liquids A10 and A11 were each heat-treated by being immersed in a water bath at 90° C. for 30 minutes together with a centrifuge tube containing the emulsified liquid.

<Preparation of Sample Liquids A10 and A11>

The emulsified liquids A10 and A11 contained in the centrifuge tubes were centrifuged at 20° C. at 12,000×g for 30 minutes so as to prepare sample liquids A10 and A11. In each sample liquid, it was confirmed that oil drops were agglomerated in the vicinity of the liquid surface of the sample liquid.

<Redispersion of Oil Drops>

The sample liquid A10 or A11 in each centrifuge tube were stirred for one minute by using a stirrer (SLOWSTIRRER BS56L), produced by IWAKI while the number of rotations was set at a scale of 3 so as to redisperse the agglomerated oil drops.

<Measurement of Redispersion>

Before and after redispersion of oil drops, a part of each of the sample liquids A10 and A11 was collected from the centrifuge tube by using a microsyringe, and it was three-fold diluted with distilled water. In each sample liquid after dilution, the average value (n=3) of the absorbance at a wavelength of 600 nm was measured by using a spectrophotometer (U-2000), produced by Hitachi, Ltd. The results are shown in Table 5 and FIG. 6(a).

TABLE 5

| | Sample liquid A10 | | |
|---|---|---|---|
| Sodium chloride concentration (mM) | 0 | | |
| Stirring time (minutes) | 0 | 1 | 2 |
| Absorbance | 0.0110 | 0.1830 | 0.1540 |

| | Sample liquid A11 | | |
|---|---|---|---|
| Sodium chloride concentration (mM) | 100 | | |
| Stirring time (minutes) | 0 | 1 | 2 |
| Absorbance | 0.0180 | 0.1410 | 0.1390 |

Figure 6A:
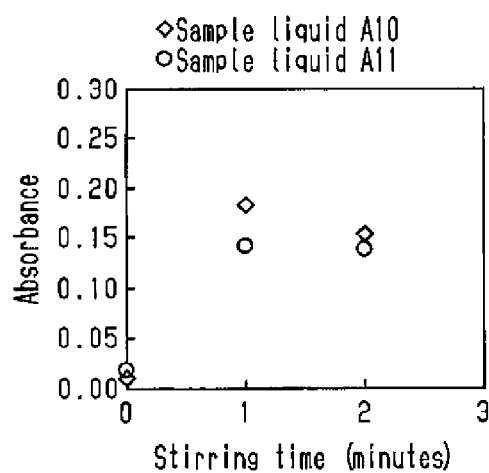
FIG. 6(a) is a graph showing the relationship between the stirring time and the absorbance in the sample liquids A10 and A11.

As is apparent from the results shown in Table 5 and FIG. 6(a), it was confirmed that by stirring the sample liquid, the absorbance of the sample liquid was increased.

EXAMPLE 6

Preparation of Suspension Liquids B1 to B4

To a sample tube, 240 µL of aqueous suspension liquid containing 2.5% by mass of solid particles of polystyrene latex having an average particle size of 0.5 µm and 960 µL of pure water were dispensed and then mixed, and thus a suspension liquid B1 containing 0.5% by mass of solid particles and having a sodium chloride concentration of 0 mM was prepared.

A sodium chloride solution was prepared by dissolving 0.366 g of sodium chloride in 50 mL of pure water. By mixing 960 µL of the sodium chloride solution with 240 µL of aqueous suspension liquid containing 2.5% by mass of solid particles of polystyrene latex having an average particle size of 0.5 µm, a suspension liquid B2 containing 0.5% by mass of solid particles and having a sodium chloride concentration of 100 mM was prepared.

A sodium chloride solution was prepared by dissolving 0.731 g of sodium chloride in 50 mL of pure water. By mixing 960 µL of the sodium chloride solution with 240 µL of aqueous suspension liquid containing 2.5% by mass of solid particles of polystyrene latex having an average particle size of 0.5 µm, a suspension liquid B3 containing 0.5% by mass of solid particles and having a sodium chloride concentration of 200 mM was prepared.

A sodium chloride solution was prepared by dissolving 1.463 g of sodium chloride in 50 mL of pure water. By mixing 960 µL of the sodium chloride solution with 240 µL of aqueous suspension liquid containing 2.5% by mass of solid particles of polystyrene latex having an average particle size of 0.5 µm, a suspension liquid B4 containing 0.5% by mass of solid particles and having a sodium chloride concentration of 400 mM was prepared.

<Preparation of Sample Liquids B1 to B4>

The suspension liquids B1 to B4 contained in the sample tubes were centrifuged at 20° C. at 1,960×g for 5 minutes and then centrifuged at 20° C. at 7,830×g for 10 minutes so as to prepare sample liquids B1 to B4. In each sample liquid, it was confirmed that solid particles were agglomerated in the liquid bottom of the sample liquid.

<Redispersion of Solid Particles>

Sinusoidal sound wave vibration at 100 Hz was applied to the sample liquids B1 to B4 in the sample tubes for 60 minutes by using a speaker (GY-1), produced by Foster Electric Company, Limited, thereby redispersing the agglomerated solid particles.

<Measurement of Redispersion>

Before and after redispersion of solid particles, a part of each of the sample liquids B1 to B4 was collected from the sample tube by using a microsyringe, and it was four-fold diluted with distilled water. In each sample liquid after dilution, the absorbance at a wavelength of 600 nm was measured by using a spectrophotometer (U-2000) produced by Hitachi, Ltd. The average value (n=3) of the differences in the absorbance of each sample liquid measured before and after the redispersion was calculated. The results are shown in Table 6 and FIG. 6(b).

TABLE 6

| | Sample liquid B1 | Sample liquid B2 | Sample liquid B3 | Sample liquid B4 |
|---|---|---|---|---|
| Sodium chloride concentration (mM) | 0 | 100 | 200 | 400 |

TABLE 6-continued

|  | Sample liquid B1 | Sample liquid B2 | Sample liquid B3 | Sample liquid B4 |
|---|---|---|---|---|
| Absorbance difference (ΔAbs) | 0.6984 | 0.4451 | 0.3468 | −0.0114 |

Figure 6B:
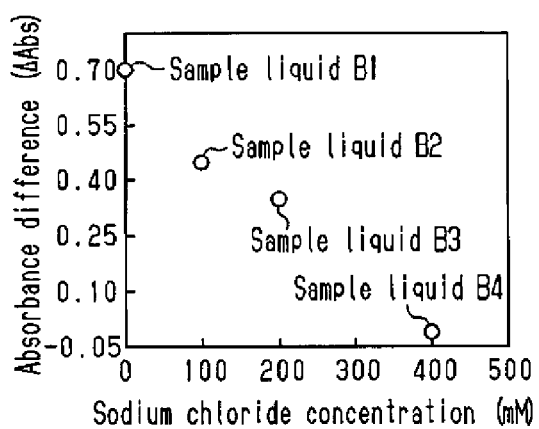
FIG. 6(b) is a graph showing the relationship between the sodium chloride concentration and the absorbance difference in the sample liquids B1 to B4.

As is apparent from the results shown in Table 6 and FIG. 6(b), it was confirmed that the sodium chloride concentration and the absorbance difference (ΔAbs) were correlated with each other. This reveals that the higher the sodium chloride concentration, the more easily an agglomerate having the stronger degree of the agglomeration is formed.

EXAMPLE 7

Preparation of Suspension Liquid B5

The suspension liquid B5 is the same as the suspension liquid B1 of Example 6. That is to say, the suspension liquid B5 was prepared by the same method as for the suspension liquid B1 in Example 6.
<Preparation of Sample Liquid B5>
The suspension liquid B5 contained in a sample tube was centrifuged at 20° C. at 1,960×g for 5 minutes and then centrifuged at 20° C. at 7,830×g for 10 minutes so as to prepare a sample liquid B5. In this sample liquid, it was confirmed that solid particles were agglomerated in the liquid bottom of the sample liquid.
<Redispersion of Solid Particles>
Sinusoidal sound wave vibration at 100 Hz was applied to the sample liquid B5 in the sample tube for 20 minutes, 40 minutes, or 60 minutes by using a speaker (GY-1), produced by Foster Electric Company, Limited, thereby redispersing the agglomerated solid particles.
<Measurement of Redispersion>
Before and after redispersion of solid particles, a part of the sample liquid B5 was collected from the sample tube by using a microsyringe, and it was four-fold diluted with distilled water. In the sample liquid after dilution, the average value (n=3) of the absorbance at a wavelength of 600 nm was measured by using a spectrophotometer (U-2000), produced by Hitachi, Ltd. The results are shown in Table 7 and FIG. 7(a).

TABLE 7

|  | Sample liquid B5 | | | |
|---|---|---|---|---|
| Sodium chloride concentration (mM) | 0 | | | |
| Vibration time (minutes) | 0 | 20 | 40 | 60 |
| Absorbance | 0.0122 | 0.1022 | 0.3584 | 0.7106 |

Figure 7A:
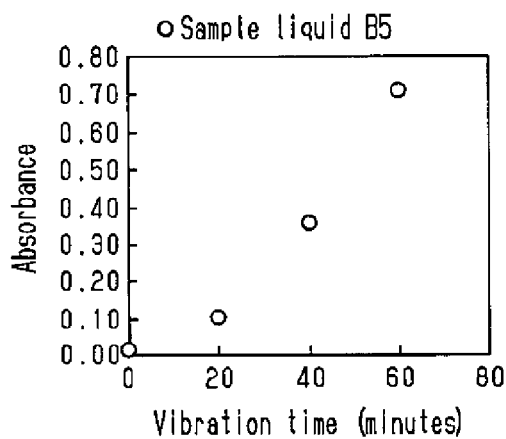
FIG. 7(a) is a graph showing the relationship between the vibration time and the absorbance in the sample liquid B5.

As is apparent from the results shown in Table 7 and FIG. 7(a), it was confirmed that the longer the time of applying vibration to the sample liquid, the higher became the absorbance of the sample liquid. With reference to FIG. 7(a), it is shown that when the vibration time was 60 minutes or less, the absorbance and the vibration time were almost directly proportional to each other. Therefore, for example, by determining the inclination of the direct proportional line by linear approximation, it is possible to evaluate the degree of agglomeration of the agglomerate in the sample liquid and the dispersion stability.

EXAMPLE 8

Preparation of Suspension Liquid B6

The suspension liquid B6 is the same as the suspension liquid B1 of Example 6. That is to say, the suspension liquid B6 was prepared by the same method as for the suspension liquid B1 in Example 6.
<Preparation of Sample Liquid B6>
The suspension liquid B6 contained in a sample tube was centrifuged at 20° C. at 1,960×g for 5 minutes and then centrifuged at 20° C. at 7,830×g for 10 minutes so as to prepare a sample liquid B6. In this sample liquid, it was confirmed that solid particles were agglomerated in the liquid bottom of the sample liquid.
<Redispersion of Solid Particles>
Rotational vibration was applied to the sample liquid B6 in the sample tube for one minute or two minutes by using a vortex mixer (Automatic Lab-mixer HM-10H), produced by IUCHI as a vibration exciter while the number of rotations was set at a scale of 3. Thus, the agglomerated solid particles were redispersed.
<Measurement of Redispersion>
Before and after redispersion of solid particles, a part of the sample liquid B6 was collected from the sample tube by using a microsyringe, and it was 32-fold diluted with distilled water. In the sample liquid after dilution, the average value (n=3) of the absorbance at a wavelength of 600 nm was measured by using a spectrophotometer (U-2000), produced by Hitachi, Ltd. The results are shown in Table 8 and FIG. 7(b).

TABLE 8

|  | Sample liquid B6 | | |
|---|---|---|---|
| Sodium chloride concentration (mM) | 0 | | |
| Vibration time (minutes) | 0 | 1 | 2 |
| Absorbance | 0.0122 | 0.2841 | 1.0978 |

Figure 7B:
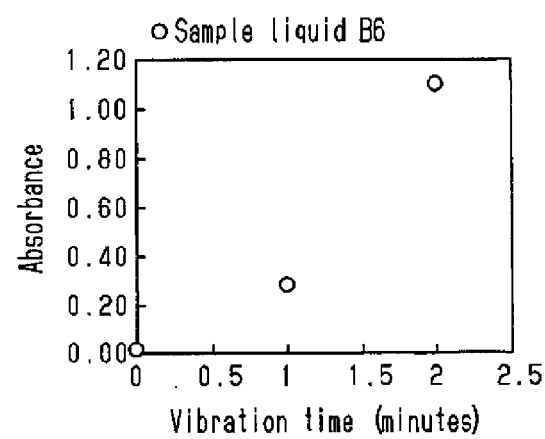
FIG. 7(b) is a graph showing the relationship between the vibration time and the absorbance in the sample liquid B6.

As is apparent from the results shown in Table 8 and FIG. 7(b), it was confirmed that the longer the time of applying vibration to the sample liquid was, the higher became the absorbance of the sample liquid.

EXAMPLE 9

Preparation of Suspension Liquids B7 to B12

To a sample tube, 60 μL of aqueous suspension liquid containing 2.5% by mass of solid particles of polystyrene latex having an average particle size of 0.5 μm and 960 μL of ion exchanged water were dispensed and then mixed. To the mixture, ion exchanged water was added so that the total amount became 1200 μL to prepare a suspension liquid B7 containing 0.125% by mass of solid particles.

A suspension liquid B8 containing 0.25% by mass of solid particles was prepared by the same method as in the method for the suspension liquid B7 except that the amount of the aqueous suspension liquid to be mixed with 960 μL of ion exchanged water was changed to 120 μL instead of 60 μL.

A suspension liquid B9 containing 0.5% by mass of solid particles was prepared by the same method as in the method for the suspension liquid B7 except that the amount of the aqueous suspension liquid to be mixed with 960 µL of ion exchanged water was changed to 240 µL instead of 60 µL.

A sodium chloride solution was prepared by dissolving 0.439 g of sodium chloride in 50 mL of pure water. This sodium chloride solution in the amount of 960 µL was mixed with 60 µL of aqueous suspension liquid containing 2.5% by mass of solid particles of polystyrene latex having an average particle size of 0.5 µm. To the mixture, ion exchanged water was added so that the total amount became 1200 µL to prepare a suspension liquid B10 containing 0.125% by mass of solid particles and having a sodium chloride concentration of 120 mM.

A suspension liquid B11 containing 0.25% by mass of solid particles and having a sodium chloride concentration of 120 mM was prepared by the same method as in the method for the suspension liquid B10 except that the amount of the aqueous suspension liquid to be mixed with 960 µL of sodium chloride solution was changed to 120 µL instead of 60 µL.

A suspension liquid B12 containing 0.5% by mass of solid particles and having a sodium chloride concentration of 120 mM was prepared by the same method as in the method for the suspension liquid B10 except that the amount of the aqueous suspension liquid to be mixed with 960 µL of sodium chloride solution was changed to 240 µL instead of 60 µL.

<Preparation of Sample Liquids B7 to B12>

The suspension liquids B7 to B12 contained in sample tubes were centrifuged at 20° C. at 1,960×g for 5 minutes and then centrifuged at 20° C. at 7,830×g for 10 minutes so as to prepare sample liquids B7 to B12. In each sample liquid, it was confirmed that solid particles were agglomerated in the liquid bottom of the sample liquid.

<Redispersion of Solid Particles>

Rotational vibration was applied to each of the sample liquids B7 to B12 in the sample tube for two minutes by using a vortex mixer (Automatic Lab-mixer HM-10H), produced by IUCHI as a vibration exciter while the number of rotations was set at a scale of 3. Thus, the agglomerated solid particles were redispersed.

<Measurement of Redispersion>

Before and after redispersion of solid particles, a part of each of the sample liquids B7 to B12 was collected from the sample tube by using a microsyringe, and it was 20-fold diluted with distilled water. In each sample liquid after dilution, the average value (n=3) of the absorbance at a wavelength of 600 nm was measured by using a spectrophotometer (U-2000) produced by Hitachi, Ltd. Furthermore, not only the absorbance of the sample liquids B7 to B12 but also the absorbance of the suspension liquids B7 to B12 was also measured. More specifically, in the absorbance of each of the suspension liquids B7 to B12 that had been 60-fold diluted with distilled water, the average value (n=3) of the absorbance at a wavelength of 600 nm was measured by using a spectrophotometer (U-2000) produced by Hitachi, Ltd. Then, the measured value of the absorbance was multiplied by three so as to obtain a value equivalent to the absorbance measured in the 20-fold diluted suspension liquids B7 to B12. The results are shown in Table 9.

TABLE 9

|  | Sample liquid B7 | Sample liquid B8 | Sample liquid B9 |
| --- | --- | --- | --- |
| Solid particle concentration (% by mass) | 0.125 | 0.25 | 0.5 |
| Sodium chloride concentration (mM) | 0 | 0 | 0 |
| Absorbance of suspension liquid | 0.678 | 0.136 | 2.726 |
| Absorbance of sample liquid | Vibration time 0 minutes | 0.014 | 0.016 | 0.021 |
| | Vibration time 2 minutes | 0.651 | 1.354 | 2.592 |
| Equivalent absorbance value | Vibration time 0 minutes | 0.021 | 0.012 | 0.008 |
| | Vibration time 2 minutes | 0.960 | 0.993 | 0.951 |
| Redispersion rate | 0.469 | 0.491 | 0.472 |
| Average value of redispersion rate | | 0.4772 | |
| Standard error | | 0.0067 | |

|  | Sample liquid B10 | Sample liquid B11 | Sample liquid B12 |
| --- | --- | --- | --- |
| Solid particle concentration (% by mass) | 0.125 | 0.25 | 0.5 |
| Sodium chloride concentration (mM) | 120 | 120 | 120 |
| Absorbance of suspension liquid | 0.629 | 1.258 | 2.516 |
| Absorbance of sample liquid | Vibration time 0 minutes | 0.012 | 0.018 | 0.020 |
| | Vibration time 2 minutes | 0.084 | 0.153 | 0.270 |
| Equivalent absorbance value | Vibration time 0 minutes | 0.019 | 0.014 | 0.008 |
| | Vibration time 2 minutes | 0.134 | 0.122 | 0.107 |
| Redispersion rate | 0.057 | 0.054 | 0.050 |
| Average value of redispersion rate | | 0.0535 | |
| Standard error | | 0.0022 | |

Figure 8:
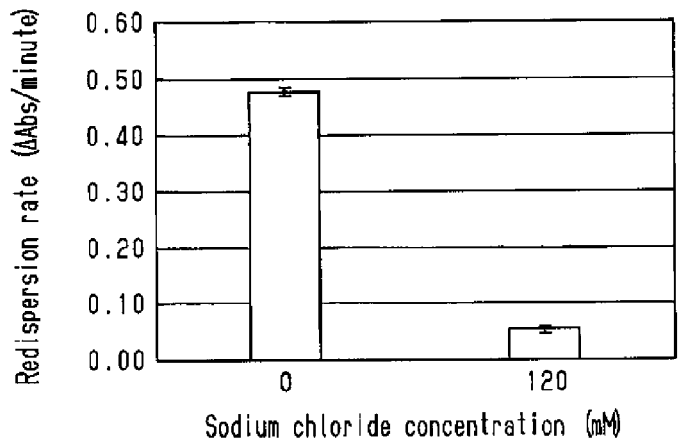
FIG. 8 is a graph showing the relationship between the sodium chloride concentration and the redispersion rate in the sample liquids B7 to B12.

In the column "equivalent absorbance value" in Table 9, the equivalent absorbance value is shown, which is obtained by converting the absorbance value of each sample liquid when the absorbance of the corresponding suspension liquid is defined as "1." Furthermore, in the "redispersion rate" column, the increased amount per minute of vibration time, which is obtained from the equivalent value of the sample liquid, is shown. FIG. 8 shows the relationship between the sodium chloride concentration and the redispersion rate. As shown in FIG. 8, it is clear that there is a difference in the redispersion rate between the case in which the sodium chloride concentration is 0 mM and the case in which the sodium chloride concentration is 120 mM. Furthermore, this result also shows that the redispersion rate has a value corresponding to the degree of agglomeration of an agglomerate without depending upon the concentration of solid particles (dispersoid).

EXAMPLE 10

Preparation of Emulsified Liquid C1

A mixture obtained by adding 14.0 g of whole milk powder to 300 mL of pure water of 60° C. was stirred and dissolved for two minutes by using a mixer to prepare an aqueous dispersion liquid of whole milk. Next, a mixture obtained by adding 0.25 g of POEM DP-95 (trade name) and 0.15 g of POEM BS-20 (trade name), both of which are emulsifiers produced by Riken Vitamin Co., Ltd., to 300 mL of pure water of 85° C. was stirred and dissolved for three minutes by using a mixer to prepare an emulsifier solution. The thus obtained aqueous dispersion liquid and emulsifier liquid were mixed with each other. To the mixture, pure water was added so that the total amount became 1000 mL, and the mixture solution was homogenized by a homogenizer. Thus, the emulsified liquid C1 was prepared. The obtained emulsified liquid C1 was heated at 121° C. for 30 minutes, which were sterilization conditions for foods, and allowed to stand still at room temperature for 24 hours. Even after still standing for 24 hours, the emulsification state of the emulsified liquid C1 was maintained.

<Preparation of Sample Liquid C1>

1.2 mL of the emulsified liquid C1 divided into in a sample tube was centrifuged at 20° C. at 140,000×g for 20 minutes so as to prepare a sample liquid C1. In this sample liquid, it was confirmed that oil drops were agglomerated in the vicinity of the liquid surface of the sample liquid.

<Redispersion of Oil Drops and Measurement of Redispersion>

Figure 9:
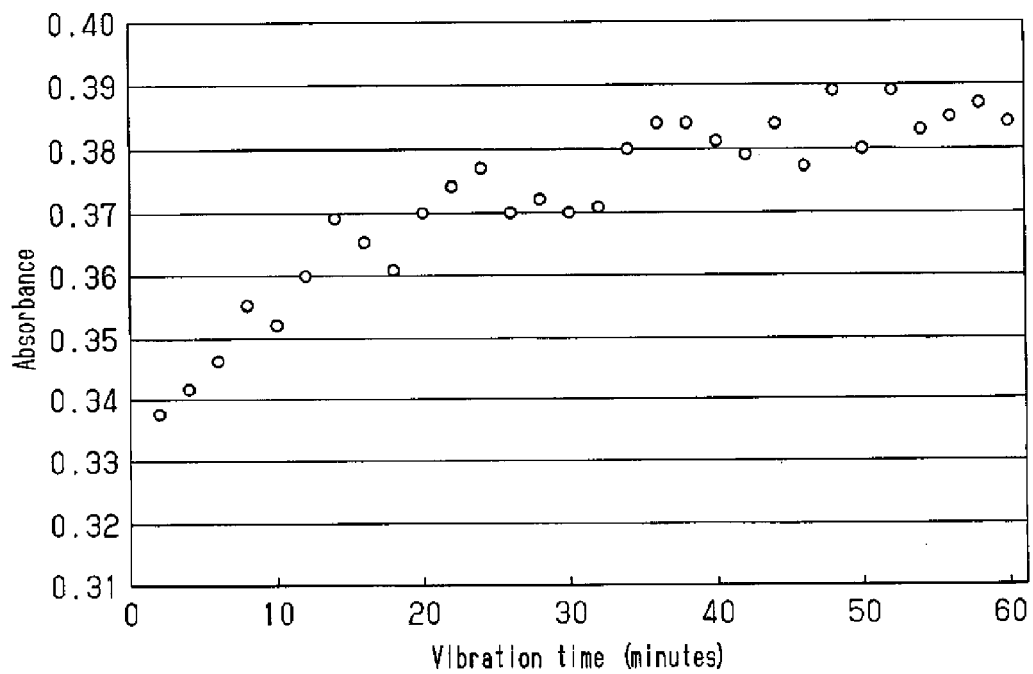
FIG. 9 is a graph showing the relationship between the vibration time and the absorbance in the sample liquid C1.

By using an analysis device shown in FIG. 3, the oil drops agglomerated in the sample liquid C1 were redispersed, and the amount of the redispersed oil drops (dispersoid) was measured. That is to say, in order to redisperse the oil drops agglomerated in the sample liquid C1, sinusoidal sound wave vibration at 100 Hz was applied to the sample liquid C1 for one hour. During this vibration time, the absorbance at a wavelength of 600 nm of the sample liquid C1 was continuously measured. The results are shown in FIG. 9. In the analysis device shown in FIG. 3, while the vibration is applied to the sample liquid, the amount of dispersoid redispersed by the applied vibration can be continuously measured.

The invention claimed is:

1. A method for evaluating the stability of a dispersion made by dispersing a liquid or solid dispersoid into a liquid dispersion medium, the method comprising:
    preparing a sample liquid from the dispersion by forming an agglomerate of the dispersoid in the dispersion medium;
    redispersing the dispersoid that forms the agglomerate in the sample liquid into the dispersion medium of the sample liquid;
    measuring a ratio of the amount of the dispersoid that has been redispersed from the agglomerate in the sample liquid with respect to the total amount of the dispersoid in the dispersion to calculate a redispersion rate from the change of the measured ratio over time; and
    evaluating the dispersion as having a higher stability as the calculated redispersion rate has a higher value.

2. The method according to claim 1, wherein the redispersing of the dispersoid is carried out by propagating vibration to the sample liquid from outside the sample liquid.

3. The method according to claim 2, wherein the vibration propagated to the sample liquid is a sinusoidal wave.

4. The method according to claim 1, wherein the preparing of a sample liquid from the dispersion is carried out by subjecting the dispersion to centrifugation.

5. A device for evaluating the stability of a dispersion by using a sample liquid, wherein the dispersion is made by dispersing a liquid or solid dispersoid into a liquid dispersion medium, and the sample liquid is prepared from the dispersion by forming an agglomerate of the dispersoid in the dispersion medium, the device comprising:
    a redispersion section for redispersing, into the dispersion medium of the sample liquid, the dispersoid that forms an agglomerate in the sample liquid; and
    a measurement section for measuring a ratio of the amount of the dispersoid that has been redispersed by the redispersion section with respect to the total amount of the dispersoid in the dispersion to calculate a redispersion rate from the change of the measured ratio over time.

* * * * *